United States Patent
Donaghy et al.

(10) Patent No.: US 12,097,378 B2
(45) Date of Patent: Sep. 24, 2024

(54) RESUSCITATION SYSTEM

(71) Applicant: HeartSine Technologies Limited, Belfast (GB)

(72) Inventors: Dymphna Mary Donaghy, County Donegal (IE); Johnny Houston Anderson, Holywood (GB); Adam Patrick Harvey, Hillsborough (GB); Peter James Lindsay, County Antrim (GB)

(73) Assignee: HEARTSINE TECHNOLOGIES LIMITED, Belfast (GB)

(*) Notice: Subject to any disclaimer, the term of this patent is extended or adjusted under 35 U.S.C. 154(b) by 316 days.

(21) Appl. No.: 17/307,203

(22) Filed: May 4, 2021

(65) Prior Publication Data
US 2021/0346708 A1    Nov. 11, 2021

(30) Foreign Application Priority Data

May 5, 2020 (GB) .................................. 2006613
Dec. 24, 2020 (GB) .................................. 2020616

(51) Int. Cl.
| | | |
|---|---|---|
| *A61N 1/39* | (2006.01) |
| *A61N 1/02* | (2006.01) |
| *G16H 20/30* | (2018.01) |
| *A61H 31/00* | (2006.01) |

(52) U.S. Cl.
CPC ........... *A61N 1/3987* (2013.01); *A61N 1/025* (2013.01); *A61N 1/39044* (2017.08); *A61N 1/3925* (2013.01); *G16H 20/30* (2018.01); *A61H 31/005* (2013.01)

(58) Field of Classification Search
CPC .......................... A61N 1/3987; A61N 1/39044
USPC .............................................................. 607/3
See application file for complete search history.

(56) References Cited

U.S. PATENT DOCUMENTS

| | | | |
|---|---|---|---|
| 2006/0271407 A1* | 11/2006 | Rosenfeld | .............. G16H 50/20 |
| | | | 434/262 |
| 2018/0339162 A1* | 11/2018 | Taylor | ................. A61N 1/3904 |

* cited by examiner

*Primary Examiner* — Nicole F Lavert
*Assistant Examiner* — Nicole F Johnson

(57) ABSTRACT

A resuscitation system for use in the resuscitation of a subject includes a computing device configured to input subject information and use the subject information to create a subject resuscitation strategy, a sensor configured to detect subject biosignals and use the subject biosignals to monitor for a subject cardiac arrest event, and a defibrillator configured to determine and deliver a subject resuscitation treatment. On determination of a subject cardiac arrest event, the sensor outputs sensor subject biosignals to the computing device. The computing device uses the sensor subject biosignals to adapt the subject resuscitation strategy and output the subject resuscitation strategy to the defibrillator. The defibrillator measures subject biodata and uses the subject biodata and the subject resuscitation strategy to determine and deliver a subject resuscitation treatment. During subject resuscitation treatment, the defibrillator repeatedly uses measured subject biodata and the subject resuscitation strategy to adapt the subject resuscitation treatment.

13 Claims, 4 Drawing Sheets

RESUSCITATION SYSTEM

CROSS-REFERENCE TO RELATED APPLICATIONS

The present disclosure claims priority benefit of United Kingdom Patent Application No. 2006613.0, filed on May 5, 2020 and United Kingdom Patent Application No. 2020616.5, filed on Dec. 24, 2020, the disclosures of which are incorporated by reference herein in their entireties.

FIELD OF THE INVENTION

The disclosure relates to a resuscitation system which uses information about a subject to determine a resuscitation strategy and adapt resuscitation treatment for the subject.

BACKGROUND

Both the European Resuscitation Council and the American Heart Association Guidelines for adult basic life support in a cardiac arrest event, suggest that a rescuer should perform the exact same actions on adult subjects, regardless of age, gender, health status, duration of cardiac arrest etc. Applying the same actions on the same subject may not represent the optimal treatment for a cardiac arrest event for a particular individual.

SUMMARY

Additional features and advantages of the invention will be set forth in the description which follows, and in part will be obvious from the description, or may be learned by practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth herein.

It has been realized that it is possible that various characteristics of respective patients could influence the condition of the subject and therefore the optimal actions a rescuer should take to achieve successful resuscitation and prevent loss of life. The present disclosure introduces a solution to this issue which includes a system for repeatedly receiving information about the patient and dynamically adjusting, based on received information, a subject resuscitation strategy and thereafter modifying a subject resuscitation treatment. The information can be received via a sensor or can be simply additional information about the patient such as age, gender, weight, etc.

An example resuscitation system for use in the resuscitation of a subject includes a computing device configured to input subject information and use the subject information to create a subject resuscitation strategy, a sensor configured to detect subject biosignals and use the subject biosignals to monitor for a subject cardiac arrest event and a defibrillator configured to determine and deliver a subject resuscitation treatment. On determination of a subject cardiac arrest event, the sensor is configured to output sensor subject biosignals to the computing device, the computing device is configured to use the sensor subject biosignals to adapt the subject resuscitation strategy and output the subject resuscitation strategy to the defibrillator, the defibrillator is configured to measure subject biodata, use the subject biodata and the subject resuscitation strategy to determine and deliver a subject resuscitation treatment. During subject resuscitation treatment, the defibrillator is configured to repeatedly measure subject biodata and output defibrillator subject biodata to the computing device. The computing device repeatedly uses the defibrillator subject biodata to adapt the subject resuscitation strategy and output the subject resuscitation strategy to the defibrillator. The defibrillator is configured to repeatedly use the measured subject biodata and the subject resuscitation strategy to adapt the subject resuscitation treatment.

The computing device can include a resuscitation strategy software algorithm which parses the subject information and uses the parsed subject information to create the subject resuscitation strategy. The resuscitation strategy software algorithm accesses a database of previously-developed resuscitation strategies categorized by subject information and selects a previously-developed resuscitation strategy that best fits the parsed subject information to be the subject resuscitation strategy.

The computing device can include a resuscitation strategy software algorithm which uses the sensor subject biosignals to adapt the subject resuscitation strategy. The resuscitation strategy software algorithm can access a database of optimal subject biosignals, determine sensor subject biosignals which are suboptimal subject biosignals, and adapt aspects of the subject resuscitation strategy corresponding to the suboptimal subject biosignals.

The computing device can further include a resuscitation strategy software algorithm which uses the defibrillator subject biodata to adapt the subject resuscitation strategy. The resuscitation strategy software algorithm accesses a database of optimal subject biodata, determines defibrillator subject biodata which are suboptimal subject biodata, and adapts aspects of the subject resuscitation strategy corresponding to the suboptimal subject biodata.

Other additional features can be included as well. A resuscitation system according to any preceding concept above can be provided in which the subject information can include any one or more of subject health data, subject genetic data, subject lifestyle data, and subject demographic data. The resuscitation system according to any concept above can include the sensor detecting subject biosignals prior to a subject cardiac arrest event and outputs the prior subject biosignals to the computing device.

A resuscitation system according to any concept above can include the sensor detecting subject biosignals including any one or more of subject heart rate signals, subject ECG (electrocardiogram) signals, subject blood pressure signals, subject respiration rate signals, subject blood oxygen saturation signals, subject activity data signals, subject position signals, and subject location signals.

A resuscitation system according to any preceding concept can include the sensor further measuring subject information about subject lifestyle changes and outputting the subject information to the computing device, which uses the subject information to adapt the subject resuscitation strategy.

A resuscitation system according to any preceding concept can include the defibrillator measuring subject biodata including any one or more of subject heart rate biodata, subject ECG biodata, subject ICG biodata, subject blood pressure biodata, subject respiration rate biodata, subject blood oxygen saturation biodata, subject cardiopulmonary resuscitation (CPR) chest compression biodata, a type of the cardiac arrest event, condition of the subject, duration of the cardiac arrest event, subject response to the resuscitation treatment, and success of resuscitation treatment. Other factors can be used by the resuscitation system as well.

A resuscitation system according to any preceding concept in which the subject resuscitation treatment can include a set of software instructions which are used by the defibrillator to alter one or more defibrillation shock waveform characteristics for the subject.

A resuscitation system can include the defibrillation shock waveform characteristics include any one or more of pulse duration, energy, voltage, tilt, and interphase spacing. Other factors can also be used by the resuscitation system.

A resuscitation system according to any preceding concept can include the subject resuscitation treatment including a set of software instructions which are used by the defibrillator to alter feedback presented to a rescuer using the defibrillator to deliver the resuscitation treatment for the subject.

The feedback can include any one or more of perform hands-only CPR, perform mouth to mouth CPR, adjust CPR chest compression duration, adjust CPR chest compression rate, adjust CPR chest compression depth, and adjust CPR chest compression recoil.

An example method embodiment includes receiving at a computing device subject information, based on the subject information, creating a subject resuscitation strategy, detecting, via a sensor, subject biosignals from a subject and monitoring, based on the subject biosignals, the subject for a subject cardiac arrest event. The method can include determining and delivering, via a defibrillator, a subject resuscitation treatment. On determination of a subject cardiac arrest event, outputting, from the sensor, sensor subject biosignals to the computing device, adapting, via the computing device and based on the sensor subject biosignals, the subject resuscitation strategy and outputting an updated subject resuscitation strategy to the defibrillator.

The method can further includes measuring, via the defibrillator, subject biodata from the subject, determining and delivering a subject resuscitation treatment based on the subject biodata and the updated subject resuscitation strategy. The method includes, during subject resuscitation treatment, repeatedly measuring, via the defibrillator, the subject biodata and outputting the subject biodata to the computing device. The method includes repeatedly adapting, via the computing device and based on the subject biodata, the subject resuscitation strategy and outputting the updated subject resuscitation strategy to the defibrillator. The method includes repeatedly adapting, via the defibrillator and based on the subject biodata and the updated subject resuscitation strategy, the subject resuscitation treatment. In another aspect, the system can stream data real-time or near real-time to another device, such as a device associated with an emergency medical service or team that is on their way to aid the patient. This streaming can be done via a wireless communication link which can be WiFi, cellular, Bluetooth or any other protocol.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only exemplary embodiments of the invention and are not therefore to be considered to be limiting of its scope, the invention will be described and explained with additional specificity and detail through the use of the accompanying drawings in which.

DETAILED DESCRIPTION

Figure 1:
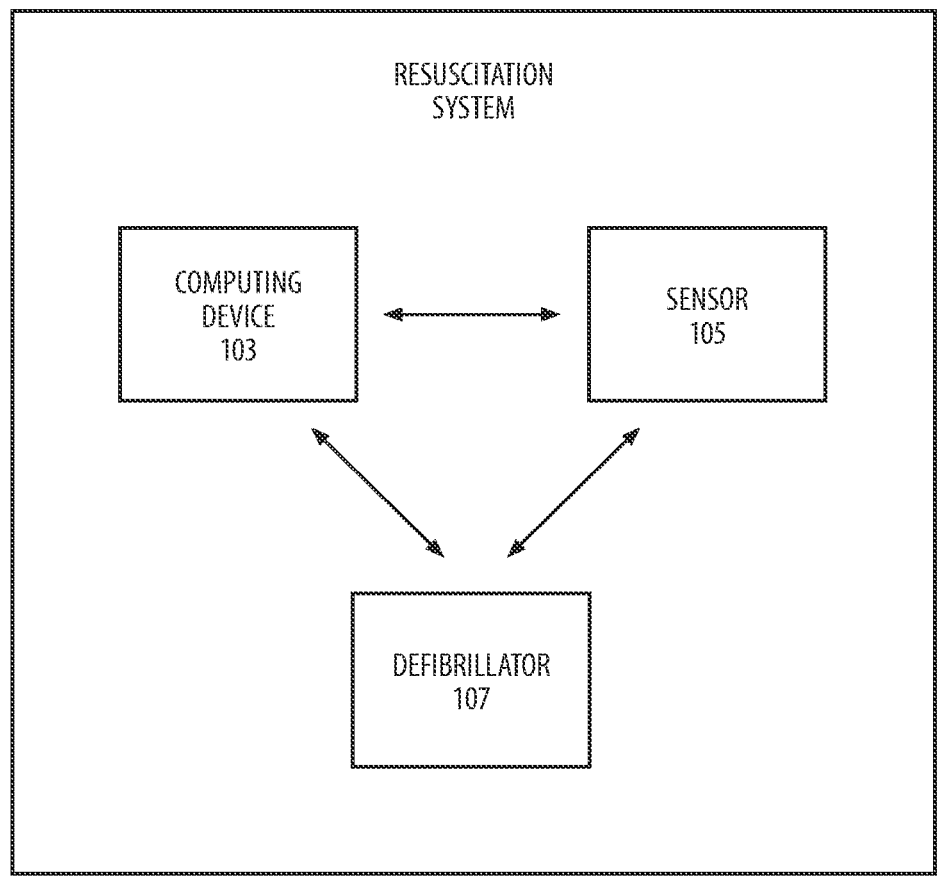
FIG. 1 illustrates an example system according to an aspect of this disclosure.

As noted above, what is needed in the art is a more dynamic and tailored treatment regime for individual patients. This disclosure introduced new concepts addressing this need. According to the disclosure, there is provided a resuscitation system for use in the resuscitation of a subject. The resuscitation system include: a computing device configured to input subject information and use the subject information to create a subject resuscitation strategy, a sensor configured to detect subject biosignals and use the subject biosignals to monitor for a subject cardiac arrest event, and a defibrillator configured to determine and deliver a subject resuscitation treatment, wherein on determination of a subject cardiac arrest event, the sensor is configured to output sensor subject biosignals to the computing device, the computing device is configured to use the sensor subject biosignals to adapt the subject resuscitation strategy and output the subject resuscitation strategy to the defibrillator, the defibrillator is configured to measure subject biodata, use the subject biodata and the subject resuscitation strategy to determine and deliver a subject resuscitation treatment, and during subject resuscitation treatment, the defibrillator is configured to repeatedly measure subject biodata and output defibrillator subject biodata to the computing device, the computing device is configured to repeatedly use the defibrillator subject biodata to adapt the subject resuscitation strategy and output the subject resuscitation strategy to the defibrillator, the defibrillator is configured to repeatedly use the measured subject biodata and the subject resuscitation strategy to adapt the subject resuscitation treatment.

The resuscitation system uses knowledge of the subject to determine best resuscitation actions to provide a tailored defibrillator resuscitation treatment for the subject. The subject knowledge comprises subject information, e.g. health records, received by the computing device, subject biosignals measured by the sensor and subject biodata measured by the defibrillator.

The computing device may include at least one processor, at least one signal transceiver, at least one storage module, at least one display module, at least one user interface. The computing device may include any of a smartphone, a tablet, a laptop. The computing device may include resuscitation strategy software. The resuscitation strategy software may include a software application.

The resuscitation strategy software may create an account for the subject. The resuscitation strategy software may link the subject information to the account. The resuscitation strategy software may link the subject resuscitation strategy to the account. The resuscitation strategy software may link the sensor subject biodata to the account. The resuscitation strategy software may link the defibrillator subject biodata to the account.

The resuscitation strategy software may include a resuscitation strategy software algorithm. The resuscitation strategy software algorithm may parse the subject information and use the parsed subject information to create the subject resuscitation strategy. The resuscitation strategy software algorithm may access a database of previously-developed resuscitation strategies categorized by subject information and select a previously-developed resuscitation strategy that best fits the parsed subject information to be the subject resuscitation strategy. The database of previously-developed resuscitation strategies may be stored in the computing device or in a remote location access by the computing device. The subject resuscitation strategy may be output to the defibrillator as a set of software instructions.

The subject information may include any of subject health data, subject genetic data, subject lifestyle data, subject demographic data. The subject health data may include any of subject medical history, subject cardiac conditions, subject health status, subject illnesses, subject injuries. The subject genetic data may include any of genetic test results, genetic variations linked to cardiac conditions, genetic variations linked to musculo-skeletal conditions. The subject lifestyle data may include any one or more of sleep data, mood data, stress level data, nutrition data, and activity data. The subject demographic data may include any one or more of height, weight, gender, ethnicity, and location data. Other data not listed can be used as well.

The computing device may input the subject information from any of the subject, a career of the subject, and medical professionals of the subject. The computing device may detect that the subject has been in a healthcare facility and input subject information including subject health data updates. The computing device may send a notification to the subject to determine if the subject wants to input the health data updates.

The computing device may receive the sensor subject biosignals and issue a notification to the sensor requesting subject health status data. The computing device may input subject health status data including subject health status good data and send a signal to the sensor causing a return to monitoring for a subject cardiac arrest event.

The computing device may treat receipt of the sensor subject biosignals as a subject cardiac arrest event alarm and send a notification to emergency services to alert them of the subject cardiac arrest event. Alternatively, on detection of a subject cardiac arrest event, the sensor may be configured to output a subject cardiac arrest event alarm and sensor subject biosignals to the computing device. The computing device may receive the subject cardiac arrest event alarm and send a notification to emergency services to alert them of the subject cardiac arrest event.

The computing device may be configured to send information about the subject to any of emergency services, a medical facility, or other location. The information about the subject may be sent in real-time during resuscitation treatment of the subject.

The sensor may be proximate the subject to detect the subject biosignals. The sensor may be a wearable sensor. The wearable sensor may be a wrist watch capable of detecting biosignals. The wearable sensor may be a chest-based device capable of detecting biosignals.

The sensor may continuously detect subject biosignals. The sensor may periodically detect subject biosignals. The sensor may detect subject biosignals prior to a subject cardiac arrest event and output the prior subject biosignals to the computing device. The subject biosignals detected prior to the subject cardiac arrest event may include biosignals detected between the subject cardiac arrest event and any of 2 hours, 1 hour, 45 mins, 30 mins, 15 mins, 10 mins, 5 mins, 3 mins prior to the subject cardiac arrest event.

The sensor may detect subject biosignals including any one or more of subject heart rate signals, subject ECG signals, subject blood pressure signals, subject respiration rate signals, subject blood oxygen saturation signals, subject regional blood oxygen saturation signals, photoplethysmography, subject activity data signals, subject position signals, and subject location signals. The sensor may detect cessation of subject heart rate signals and use this to determine a subject cardiac arrest event. The sensor may by detect an arrhythmia in subject ECG signals and use this to determine a subject cardiac arrest event.

The resuscitation strategy software algorithm of the computing device may use the sensor subject biosignals to adapt the subject resuscitation strategy. The resuscitation strategy software algorithm may access a database of optimal subject biosignals, determine sensor subject biosignals which are suboptimal subject biosignals, and adapt aspects of the subject resuscitation strategy corresponding to the suboptimal subject biosignals.

On determination of a subject cardiac arrest event, the sensor may be configured to repeatedly output sensor subject biosignals to the computing device, and the computing device may be configured to repeatedly use the sensor subject biosignals to adapt the subject resuscitation strategy and output the subject resuscitation strategy to the defibrillator. The computing device may be configured to repeatedly use the sensor subject biosignals and the defibrillator subject biodata to adapt the subject resuscitation strategy and output the subject resuscitation strategy to the defibrillator.

The sensor may further measure subject information about subject lifestyle changes and output the subject information to the computing device. The computing device may use the subject information to adapt the subject resuscitation strategy. The subject lifestyle changes may comprise any of changes in exercise routine, changes in sleep habits, changes in nutritional status.

The defibrillator may measure subject biodata including any one or more of subject heart rate biodata, subject ECG biodata, subject ICG biodata, subject blood pressure biodata, subject respiration rate biodata, subject blood oxygen saturation biodata, subject cardiopulmonary resuscitation (CPR) chest compression biodata, a type of the cardiac arrest event, condition of the subject, duration of the cardiac arrest event, subject response to the resuscitation treatment, success of resuscitation treatment.

The defibrillator may include a resuscitation treatment algorithm which uses the subject biodata and the subject resuscitation strategy to determine and deliver the subject resuscitation treatment. The subject resuscitation treatment may include a set of software instructions which are used by the defibrillator to alter one or more defibrillation shock waveform characteristics for the subject. The defibrillation shock waveform characteristics may include any one or more of pulse duration, energy, voltage, tilt, interphase spacing, and other factors. The subject resuscitation treatment may include a set of software instructions which are used by the defibrillator to alter feedback presented to a rescuer using the defibrillator to deliver the resuscitation treatment for the subject. The feedback may include any one or more of perform hands-only CPR, perform mouth to mouth CPR, adjust CPR chest compression duration, adjust CPR chest compression rate, adjust CPR chest compression depth, adjust CPR chest compression recoil, and other factors. The feedback may include prompts to the rescuer comprising any of audio prompts, visual prompts, haptic prompts, other sensory prompts.

The resuscitation strategy software algorithm of the computing device may use the defibrillator subject biodata to adapt the subject resuscitation strategy. The resuscitation strategy software algorithm may access a database of optimal subject biodata, determine defibrillator subject biodata which are suboptimal subject biodata, and adapt aspects of the subject resuscitation strategy corresponding to the suboptimal subject biodata.

The defibrillator may include a receiver configured to receive subject information from the rescuer. The subject information from the rescuer may include any one or more of subject gender, subject ethnicity, subject height, subject weight, and other factors. The defibrillator may output the subject information to the computing device. The computing device may use the subject information to adapt the subject resuscitation strategy and output the subject resuscitation strategy to the defibrillator.

The resuscitation system may be deployed in the subject's home using a home defibrillator. The resuscitation system may be deployed outside of the subject's home using a public defibrillator. The defibrillator may be an automated external defibrillator (AED).

An embodiment of the disclosure will now be described, by way of example only, with reference to the accompanying drawings, which is a schematic representation of a resuscitation system.

Referring to the drawing, a resuscitation system 100 for use in the resuscitation of a subject, includes a computing device 103, a sensor 105 and a defibrillator 107. The computing device 103, sensor 105 and defibrillator 107 are connected to each other, preferably wirelessly, but it will be appreciated that, in some circumstances, wired connections could be used.

In this embodiment, the computing device 103 includes a smartphone. The smartphone includes at least one processor, at least one signal transceiver, a resuscitation strategy software in the form of a software application, at least one storage module, at least one display module and at least one user interface.

On receipt of the resuscitation system 100, the resuscitation strategy software of the computing device 103 is used to create an account for the subject on the computing device 103. The sensor 105 and the defibrillator are linked to the subject account. When subject information is received by the computing device 103, this is linked to the subject account. When the subject resuscitation strategy is created, this is also linked to the subject account.

The computing device 103 inputs subject information and uses the subject information to create a subject resuscitation strategy. The resuscitation strategy software includes a resuscitation strategy software algorithm which parses the subject information and uses the parsed subject information to create the subject resuscitation strategy. The resuscitation strategy software algorithm accesses a database of previously-developed resuscitation strategies categorized by subject information and selects a previously-developed resuscitation strategy that best fits the parsed subject information to be the subject resuscitation strategy. The database of previously-developed resuscitation strategies may be stored in the computing device or in a remote location access by the computing device. The subject resuscitation strategy is output to the defibrillator as a set of software instructions.

The subject information input by the computing device 103 includes any one or more of subject health data, subject genetic data, subject lifestyle data, subject demographic data. The subject health data may include any of subject medical history, subject cardiac conditions, subject health status, subject illnesses, subject injuries. The subject genetic data may comprise any of genetic test results, genetic variations linked to cardiac conditions, genetic variations linked to musculo-skeletal conditions. The subject lifestyle data may include any of sleep data, mood data, stress level data, nutrition data, activity data. The subject demographic data may comprise any of height, weight, gender, ethnicity, location data.

The subject information may be input by the computing device 103 from any of the subject, a career of the subject, medical professionals of the subject. The computing device 103 may detect that the subject has been in a healthcare facility and input subject information comprising subject health data updates. The computing device 103 may send a notification to the subject to determine if the subject wants to input the health data updates.

In this embodiment, the sensor 105 is a wearable sensor, such as a wrist watch or a chest-based sensor. The sensor 105 is configured to detect subject biosignals and use the subject biosignals to monitor for a subject cardiac arrest event. The sensor 105 may continuously or periodically detect subject biosignals. The sensor 105 may detect subject biosignals prior to a subject cardiac arrest event. The subject biosignals detected prior to the subject cardiac arrest event may include biosignals detected between the subject cardiac arrest event and any of 2 hours, 1 hour, 45 mins, 30 mins, 15 mins, 10 mins, 5 mins, 3 mins prior to the subject cardiac arrest event. Other times can also be used as well as these are only exemplary.

The sensor 105 detects subject biosignals including any of subject heart rate signals, subject ECG signals, subject blood pressure signals, subject respiration rate signals, subject blood oxygen saturation signals, subject activity data signals, subject position signals, subject location signals. The sensor 105 detects cessation of subject heart rate signals and uses this to determine a subject cardiac arrest event. The sensor 105 detects an arrhythmia in subject ECG signals and uses this to determine a subject cardiac arrest event.

On determination of a subject cardiac arrest event, the sensor 105 is configured to output sensor subject biosignals to the computing device 103. The subject biosignals may be biosignals detected prior to a subject cardiac arrest event.

The computing device 105 treats receipt of the sensor subject biosignals as a subject cardiac arrest event alarm and sends a notification to emergency services to alert them of the subject cardiac arrest event. The resuscitation strategy software of the computing device 103 links the sensor subject biodata to the subject account.

The computing device 103 is configured to use the sensor subject biosignals to adapt the subject resuscitation strategy and output the subject resuscitation strategy to the defibrillator 107. The resuscitation strategy software algorithm of the computing device 103 uses the sensor subject biosignals to adapt the subject resuscitation strategy. The resuscitation strategy software algorithm accesses a database of optimal subject biosignals, determines sensor subject biosignals which are suboptimal subject biosignals, and adapts aspects of the subject resuscitation strategy corresponding to the suboptimal subject biosignals. For example, the resuscitation strategy software algorithm may determine sensor subject biosignals relating to the subject heart rate are suboptimal and adapt an aspect of the subject resuscitation strategy relating to rate of CPR to be delivered to the subject.

In this embodiment, the defibrillator 107 is an AED and the resuscitation system 1 is deployed in the subject's home using a home AED.

The defibrillator 107 is configured to measure subject biodata, use the subject biodata and the subject resuscitation strategy received from the computing device 103 to determine and deliver a subject resuscitation treatment. The defibrillator 107 measures subject biodata comprising any of subject heart rate biodata, subject ECG biodata, subject ICG biodata, subject blood pressure biodata, subject respiration rate biodata, subject blood oxygen saturation biodata, subject cardiopulmonary resuscitation (CPR) chest compression biodata. The defibrillator 107 further measures subject biodata including any of a type of the cardiac arrest event, condition of the subject, duration of the cardiac arrest event, subject response to the resuscitation treatment, and success of resuscitation treatment.

The defibrillator 107 comprises a resuscitation treatment algorithm which uses the subject biodata and the subject resuscitation strategy to determine and deliver the subject resuscitation treatment. The subject resuscitation treatment includes a set of software instructions which are used by the defibrillator to alter one or more defibrillation shock waveform characteristics for the subject. The defibrillation shock waveform characteristics may include any of pulse duration, energy, voltage, tilt, interphase spacing. The subject resuscitation treatment further includes a set of software instructions which are used by the defibrillator to alter feedback presented to a rescuer using the defibrillator to deliver the resuscitation treatment for the subject. The feedback may include any of perform hands-only CPR, perform mouth to mouth CPR, adjust CPR chest compression duration, adjust CPR chest compression rate, adjust CPR chest compression depth, adjust CPR chest compression recoil. The feedback may include prompts to the rescuer including any of audio prompts, visual prompts, haptic prompts, other sensory prompts.

During subject resuscitation treatment delivered by the defibrillator 107, the defibrillator 107 is configured to repeatedly measure subject biodata and output defibrillator subject biodata to the computing device 103. The resuscitation strategy software of the computing device 103 links the defibrillator subject biodata to the subject account. The computing device 103 is configured to repeatedly use the defibrillator subject biodata to adapt the subject resuscitation strategy. The resuscitation strategy software algorithm of the software of the computing device 103 accesses a database of optimal subject biodata, determines defibrillator subject biodata which are suboptimal subject biodata, and adapts aspects of the subject resuscitation strategy corresponding to the suboptimal subject biodata. For example, the resuscitation strategy software algorithm may determine defibrillator subject biodata relating to the subject ECG are suboptimal and adapt an aspect of the subject resuscitation strategy relating to a tilt characteristic of a defibrillation shock waveform to be delivered to the subject. The computing device 103 outputs the subject resuscitation strategy to the defibrillator 107, which uses the measured subject biodata and the subject resuscitation strategy to adapt the subject resuscitation treatment. This process is carried out repeatedly during subject resuscitation treatment, for example, the defibrillator may output defibrillator subject biodata to the computing device 103 every 5 seconds. The process can occur at regular intervals or at variable intervals based on some criteria.

The defibrillator 107 may comprise a receiver (not shown) configured to receive subject information from the rescuer, such as subject gender, subject ethnicity, subject height, subject weight. The defibrillator 107 may output the subject information to the computing device 103 and the computing device 103 may use the subject information to adapt the subject resuscitation strategy and output the subject resuscitation strategy to the defibrillator 107.

Figure 2:
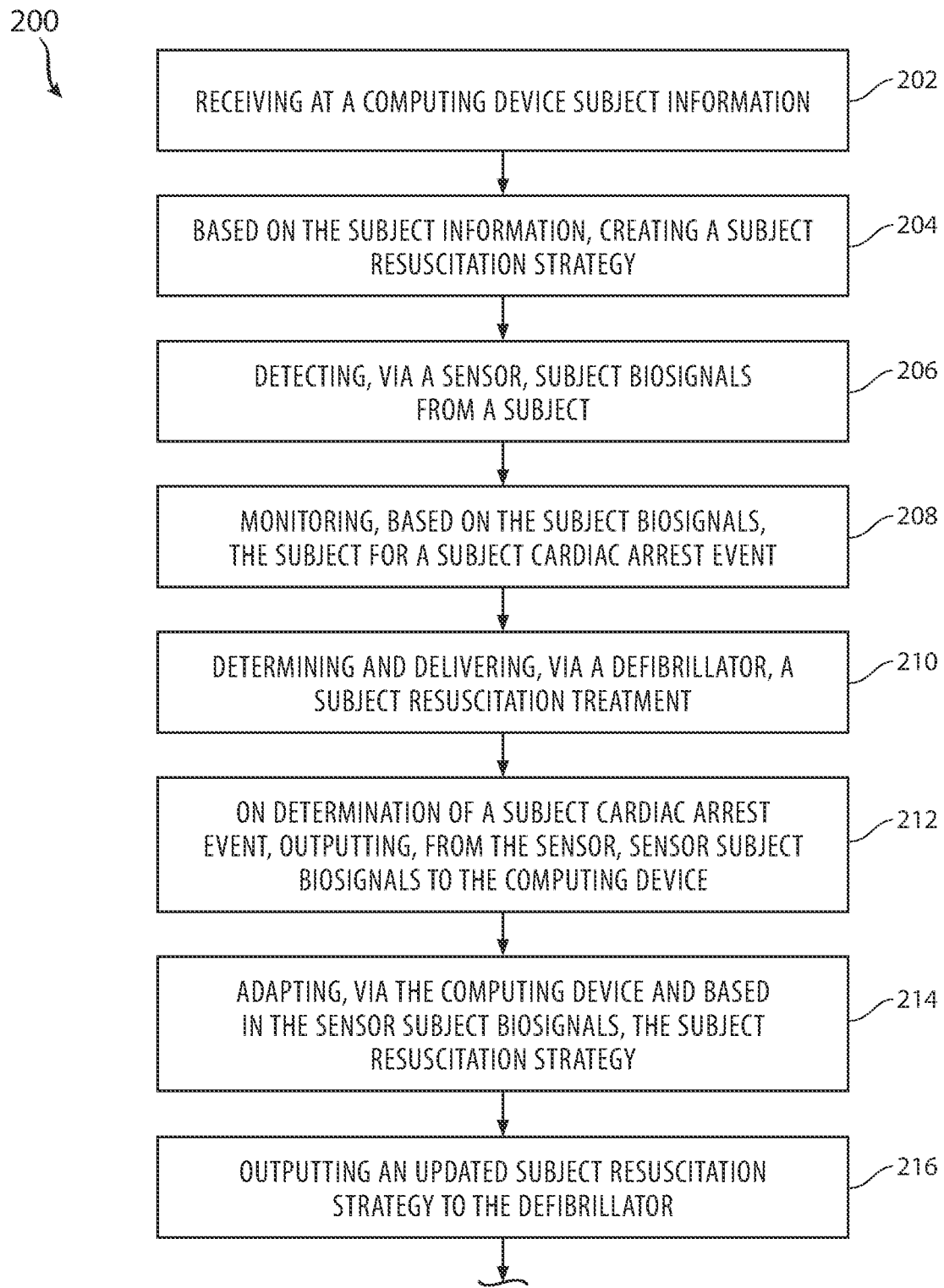
FIG. 2 illustrates a method example.
Figure 2:
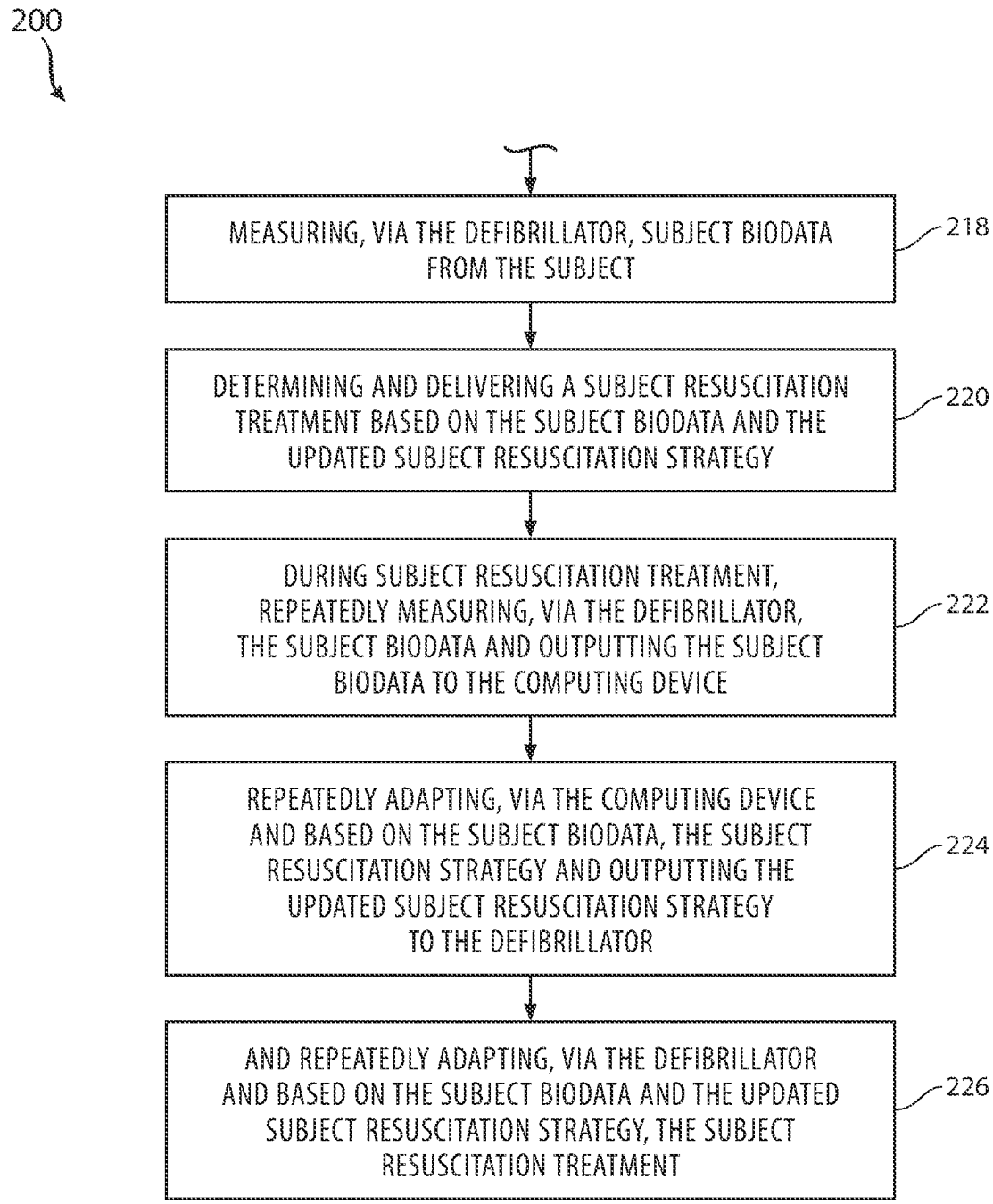

The computing device 103 is configured to send information about the subject to any of emergency services, a medical facility, in real-time, during subject resuscitation treatment. FIG. 2 illustrates an example method 200 according to an aspect of this disclosure. The method can include any one or more of the following steps in any order. The method 200 can include receiving at a computing device subject information (202), based on the subject information, creating a subject resuscitation strategy (204), detecting, via a sensor, subject biosignals from a subject (206) and monitoring, based on the subject biosignals, the subject for a subject cardiac arrest event (208). The method can include determining and delivering, via a defibrillator, a subject resuscitation treatment (210).

On determination of a subject cardiac arrest event, the method includes outputting, from the sensor, sensor subject biosignals to the computing device (212), adapting, via the computing device and based in the sensor subject biosignals, the subject resuscitation strategy (214) and outputting an updated subject resuscitation strategy to the defibrillator (216). The method can further include measuring, via the defibrillator, subject biodata from the subject (218), determining and delivering a subject resuscitation treatment based on the subject biodata and the updated subject resuscitation strategy (220). The method includes, during subject resuscitation treatment, repeatedly measuring, via the defibrillator, the subject biodata and outputting the subject biodata to the computing device (222).

The method includes repeatedly adapting, via the computing device and based on the subject biodata, the subject resuscitation strategy and outputting the updated subject resuscitation strategy to the defibrillator (224). The method includes repeatedly adapting, via the defibrillator and based on the subject biodata and the updated subject resuscitation strategy, the subject resuscitation treatment (226). While the term "updated" subject resuscitation strategy can be used, the use of "the" subject resuscitation strategy can refer both to an original strategy, or a current strategy or an updated subject resuscitation strategy. The context in which the term "the subject resuscitation strategy" is used, should make clear which meaning applies. Similarly, the use of the term "the subject resuscitation treatment" can refer to a current treatment, or an updated treatment from a previous treatment as would be made clear by the context.

The method can also include transmitting data associated with the subject or the subject resuscitation treatment to a device associated with emergency medical services. The data can be any data, a subset of data, or the same data to the device associated with the emergency medical service, such as to an ambulance or paramedic, such that the data can be used to prepare emergency personnel to have an advanced understanding of the medical condition of the patient. The data can be transmitted by cellular, WiFi, Bluetooth, wired, or in any manner that would be known to those of skill in the art. The data can also be transmitted in real-time as it is received via sensor or otherwise, or determined by the system, or the data can be in near-real time as well.

The method can also include less steps or only some of the steps outlined above. For example, the method may include receiving some biosignals from the patient, establishing a subject resuscitation treatment, then receiving additional data. Based on the additional data, the subject resuscitation treatment can be updated or change in some fashion to be configured more for the respective patient.

In one example, a method can include detecting, via a sensor, subject biosignals from a subject, monitoring, based on the subject biosignals, the subject for a subject cardiac arrest event, determining and delivering, via a defibrillator and based on the subject cardiac arrest event, a subject resuscitation treatment, during the subject resuscitation treatment, repeatedly measuring, via the defibrillator, subject biodata and repeatedly adapting, via the defibrillator and based on the subject biodata, the subject resuscitation treatment. Other examples of utilizing a subset of the steps disclosed herein to provide a particular method can be provided as well.

Figure 3:
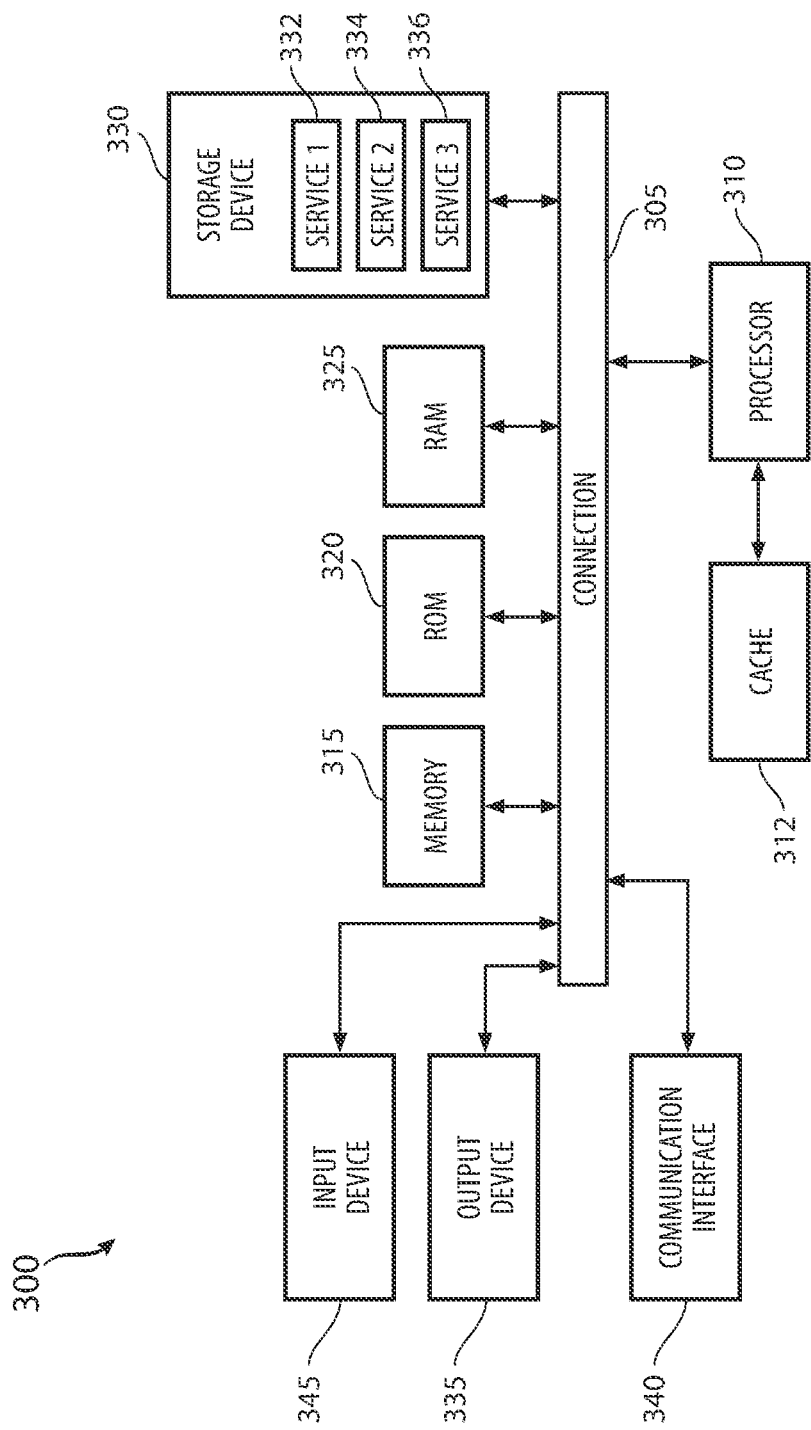
FIG. 3 illustrates an example computer system according to an aspect of this disclosure.

FIG. 3 illustrates an example computing device architecture 300 of an example computing device which can implement the various concepts described herein. The components of the computing device architecture 300 are shown in electrical communication with each other using a connection 305, such as a bus. The example computing device architecture 300 includes a processing unit (CPU or processor) 310 and a computing device connection 305 that couples various computing device components including the computing device memory 315, such as read only memory (ROM) 320 and random access memory (RAM) 325, to the processor 310.

The computing device architecture 300 can include a cache of high-speed memory connected directly with, in close proximity to, or integrated as part of the processor 310. The computing device architecture 300 can copy data from the memory 315 and/or the storage device 330 to the cache 312 for quick access by the processor 310. In this way, the cache can provide a performance boost that avoids processor 310 delays while waiting for data. These and other modules can control or be configured to control the processor 310 to perform various actions. Other computing device memory 315 may be available for use as well. The memory 315 can include multiple different types of memory with different performance characteristics. The processor 310 can include any general purpose processor and a hardware or software service, such as service 1 332, service 2 334, and service 3 336 stored in storage device 330, configured to control the processor 310 as well as a special-purpose processor where software instructions are incorporated into the processor design. A general purpose computer programmed as described herein becomes a special-purpose computer to perform the disclosed functions. The service 1, service 2 and service 3 can also represent one or more management modules that are programmed to implement the functions and operations disclosed herein. The processor 310 may be a self-contained system, containing multiple cores or processors, a bus, memory controller, cache, etc. A multi-core processor may be symmetric or asymmetric.

To enable user interaction with the computing device architecture 300, an input device 345 can represent any number of input mechanisms, such as a microphone for speech, a touch-sensitive screen for gesture or graphical input, keyboard, mouse, motion input, and so forth. The input can also include sensor input or biosignal input as described herein. An output device 335 can also be one or more of a number of output mechanisms known to those of skill in the art, such as a display, projector, television, speaker device, etc. In some instances, multimodal computing devices can enable a user to provide multiple types of input to communicate with the computing device architecture 300. The communications interface 340 can generally govern and manage the user input and computing device output. There is no restriction on operating on any particular hardware arrangement and therefore the basic features here may easily be substituted for improved hardware or firmware arrangements as they are developed.

Storage device 330 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 325, read only memory (ROM) 320, and hybrids thereof. The storage device 330 can include services 332, 334, 336 for controlling the processor 310. Other hardware or software modules are contemplated. The storage device 330 can be connected to the computing device connection 305. In one aspect, a hardware module that performs a particular function can include the software component stored in a computer-readable medium in connection with the necessary hardware components, such as the processor 310, connection 305, output device 335, and so forth, to carry out the function.

For clarity of explanation, in some instances the present technology may be presented as including individual functional blocks including functional blocks including devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can include, for example, instructions and data which cause or otherwise configure a general purpose computer, special purpose computer, special purpose processing device, a defibrillator, a sensor, and so forth, to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Some examples of such form factors include general purpose computing devices such as servers, rack mount devices, desktop computers, laptop computers, and so on, or general purpose mobile computing devices, such as tablet computers, smart phones, personal digital assistants, wearable devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" a set indicates that one member of the set or multiple members of the set satisfy the claim. For example, claim language reciting "at least one of A and B" means A, B, or A and B.

While various flow diagrams provided and described above may show a particular order of operations performed by certain embodiments of the disclosure, it should be understood that such order is exemplary (e.g., alternative embodiments can perform the operations in a different order, combine certain operations, overlap certain operations, etc.).

We claim:

1. A resuscitation system for use in a resuscitation of a subject, the resuscitation system comprising:
a computing device configured to input subject information and use the subject information to create a subject resuscitation strategy, wherein the subject information comprises previously-recorded subject health data comprising any one or more of subject genetic data, subject lifestyle data, and subject demographic data, subject medical history, a subject cardiac condition, a subject health status, a subject illness, or a subject injury;
a sensor configured to detect subject biosignals and use the subject biosignals to monitor for a subject cardiac arrest event; and
a defibrillator configured to determine and deliver a subject resuscitation treatment, wherein:
on determination of a subject cardiac arrest event, the sensor is configured to output sensor subject biosignals to the computing device, the computing device is configured, based on one or more of the sensor subject biosignals, the subject information or a combination of the sensor subject biosignals and the subject information, to adapt the subject resuscitation strategy and output an updated subject resuscitation strategy to the defibrillator, the defibrillator is configured to measure subject biodata, use the subject biodata and the updated subject resuscitation strategy to determine and deliver a subject resuscitation treatment, and during a delivery of the subject resuscitation treatment, the defibrillator is configured to repeatedly measure additional subject biodata and repeatedly output the additional subject biodata to the computing device;
the computing device is configured to repeatedly use the additional subject biodata and the previously-recorded subject health data to adapt the updated subject resuscitation strategy and output a repeatedly updated subject resuscitation strategy to the defibrillator;
the defibrillator is configured to repeatedly use the subject biodata and the repeatedly updated subject resuscitation strategy to adapt the subject resuscitation treatment; and
the computing device comprises a resuscitation strategy software algorithm which accesses a database of optimal subject biosignals, determines sensor subject biosignals which are suboptimal subject biosignals, and adapts aspects of the subject resuscitation strategy or the updated subject resuscitation strategy corresponding to the suboptimal subject biosignals.

2. A resuscitation system according to claim 1, wherein the computing device comprises a resuscitation strategy software algorithm which parses the subject information to yield parsed subject information and uses the parsed subject information to create the subject resuscitation strategy.

3. A resuscitation system according to claim 2, wherein the resuscitation strategy software algorithm accesses a database of previously-developed resuscitation strategies categorized by subject information and selects a previously-developed resuscitation strategy that best fits the parsed subject information to be the subject resuscitation strategy.

4. A resuscitation system according to claim 1, wherein the resuscitation strategy software algorithm uses the additional subject biodata to adapt the subject resuscitation strategy.

5. A resuscitation system according to claim 1, wherein the defibrillator measures subject biodata comprising any one or more of subject heart rate biodata, subject ECG biodata, subject ICG biodata, subject blood pressure biodata, subject respiration rate biodata, subject blood oxygen saturation biodata, subject cardiopulmonary resuscitation (CPR) chest compression biodata, a type of the subject cardiac arrest event, condition of the subject, duration of the subject cardiac arrest event, subject response to the subject resuscitation treatment, and a success of the subject resuscitation treatment.

6. A resuscitation system according to claim 1, wherein the subject resuscitation treatment comprises a set of software instructions which are used by the defibrillator to alter one or more defibrillation shock waveform characteristics for the subject.

7. A resuscitation system according to claim 6, wherein the defibrillation shock waveform characteristics comprise any one or more of energy, voltage, tilt, interphase spacing.

8. A resuscitation system according to claim 1, wherein the subject resuscitation treatment comprises a set of software instructions which are used by the defibrillator to alter feedback presented to a rescuer using the defibrillator to deliver the subject resuscitation treatment.

9. A resuscitation system according to claim 8, wherein the feedback comprises any one or more of perform hands-only CPR, perform mouth to mouth CPR, adjust CPR chest compression duration, adjust CPR chest compression rate, adjust CPR chest compression depth, and adjust CPR chest compression recoil.

10. A method comprising:
receiving, at a computing device, subject information, wherein the subject information comprises previously-recorded subject health data comprising one or more of subject genetic data, subject lifestyle data, subject demographic data, subject medical history, a subject cardiac condition, a subject health status, a subject illness, or a subject injury;
based on the subject information, creating, via the computing device, a first subject resuscitation strategy;
detecting, via a sensor, subject biosignals from a subject;
monitoring, based on the subject biosignals, the subject for a subject cardiac arrest event;
determining and delivering, via a defibrillator, a subject resuscitation treatment;
on determination of the subject cardiac arrest event, outputting, from the sensor, sensor subject biosignals to the computing device;

adapting, via the computing device and based on one or more of the sensor subject biosignals, the subject information or a combination of the sensor subject biosignals and the subject information, the first subject resuscitation strategy to generate an updated subject resuscitation strategy;

outputting, from the computing device, the updated subject resuscitation strategy to the defibrillator;

measuring, via the defibrillator, subject biodata from the subject;

determining and delivering the subject resuscitation treatment based on the subject biodata and the updated subject resuscitation strategy;

during a delivery of the subject resuscitation treatment, repeatedly measuring, via the defibrillator, additional subject biodata and outputting the additional subject biodata to the computing device;

accessing a database of optimal subject biodata;

determining defibrillator sensor subject biodata which are suboptimal subject biodata;

repeatedly adapting, via the computing device and based on the additional subject biodata and based on the suboptimal subject biodata, the updated subject resuscitation strategy and outputting a repeatedly updated subject resuscitation strategy to the defibrillator; and repeatedly adapting, via the defibrillator and based on the additional subject biodata and the repeatedly updated subject resuscitation strategy, the subject resuscitation treatment.

11. A method comprising:
detecting, via a sensor, subject biosignals from a subject;
monitoring, based on the subject biosignals, the subject for a subject cardiac arrest event;
determining and delivering, via a defibrillator and based on the subject cardiac arrest event and based on subject information comprising previously-recorded subject health data comprising any one or more of subject genetic data, subject lifestyle data, subject demographic data, subject medical history, a subject cardiac condition, a subject health status, a subject illness, or a subject injury, a subject resuscitation treatment;
during the subject resuscitation treatment, repeatedly measuring, via the defibrillator, subject biodata to generate repeatedly-measured subject biodata;
accessing a database of optimal subject biodata;
determining defibrillator sensor subject biodata which are suboptimal subject biodata; and
repeatedly adapting, via the defibrillator and based on one or more of the repeatedly-measured subject biodata and the suboptimal subject biodata, the subject information or a combination of the repeatedly-measured subject biodata and the subject information, the subject resuscitation treatment.

12. The method of claim 11, further comprising:
transmitting data associated with the subject or the subject resuscitation treatment to a device associated with emergency medical services.

13. The method of claim 12, wherein the transmitting of the data occurs in real-time or near-real-time.

* * * * *